(12) United States Patent
Jones et al.

(10) Patent No.: US 7,837,660 B2
(45) Date of Patent: Nov. 23, 2010

(54) RECESSED ELECTRODES FOR SENSING FLOW IN OPHTHALMIC SURGICAL SYSTEM

(76) Inventors: Ross Peter Jones, 84 Wulfstan Way, Cambridge CB1 8QH (GB); Mark Ian Lutwyche, 1008 Green Hill Farm Rd., Reisterstown, MD (US) 21136; David Martin Pooley, 1 Heffer Close, Cambridge CB22 5EB (GB)

( * ) Notice: Subject to any disclaimer, the term of this patent is extended or adjusted under 35 U.S.C. 154(b) by 143 days.

(21) Appl. No.: 11/957,841

(22) Filed: Dec. 17, 2007

(65) Prior Publication Data
US 2009/0157001 A1    Jun. 18, 2009

(51) Int. Cl.
*A61M 1/00* (2006.01)
(52) U.S. Cl. .................... 604/317; 73/861.12
(58) Field of Classification Search ............. 604/19, 604/118, 317, 20–22, 119–121; 73/861.12
See application file for complete search history.

(56) References Cited

U.S. PATENT DOCUMENTS

| | | | | |
|---|---|---|---|---|
| 4,626,248 | A * | 12/1986 | Scheller | 604/319 |
| 4,758,220 | A * | 7/1988 | Sundblom et al. | 604/65 |
| 4,758,238 | A * | 7/1988 | Sundblom et al. | 604/319 |
| 5,544,532 | A | 8/1996 | Brown | |
| 5,672,831 | A * | 9/1997 | Codina et al. | 73/861.12 |
| 6,589,237 | B2 * | 7/2003 | Woloszko et al. | 606/41 |
| 6,599,277 | B2 | 7/2003 | Neubert | 604/317 |
| 6,634,237 | B2 | 10/2003 | Neubert | 73/861.12 |
| 7,241,293 | B2 * | 7/2007 | Davison | 606/41 |
| 2003/0216725 | A1 * | 11/2003 | Woloszko et al. | 606/41 |
| 2004/0040385 | A1 * | 3/2004 | Hofmann et al. | 73/861.08 |
| 2007/0022823 | A1 * | 2/2007 | Knill et al. | 73/861.12 |

FOREIGN PATENT DOCUMENTS

WO    WO 03/047652    6/2003

OTHER PUBLICATIONS

International Search Report (PCT/ISA/210) and Written Opinion (PCT/ISA/237) mailed on Nov. 2, 2009.

* cited by examiner

*Primary Examiner*—Nicholas D Lucchesi
*Assistant Examiner*—Gerald Landry, II
(74) *Attorney, Agent, or Firm*—Jeffrey B Powers

(57) ABSTRACT

A flow measurement device 100 is provided that includes an electrode terminal chamber 102 with an inlet 104 in communication with a flow channel 108 for receiving fluid and viscoelastic material aspirated from a surgical site, and an outlet 106 that tapers into a flow channel 108. The outlet 108 has a taper angle that is sufficient to smooth flow and cause viscoelastic material entering the electrode terminal chamber 102 to flow substantially within a center portion of the chamber and through the outlet 106. The electrode terminal chamber 102 further includes first and second electrode terminals 130 and 140 disposed on generally opposite sides of the electrode terminal chamber 102 in a spaced-apart manner. The first and second electrode terminals 130 and 140 are positioned a distance from the center of the chamber 102 that is sufficient to substantially avoid contact between the terminals and viscoelastic materials flowing through the chamber 102.

20 Claims, 3 Drawing Sheets

RECESSED ELECTRODES FOR SENSING FLOW IN OPHTHALMIC SURGICAL SYSTEM

FIELD

The present invention relates to sensing an aspiration flow rate in a surgical pump system. More particularly, the present application is directed towards a flow sensor for use with surgical pump systems.

BACKGROUND

The statements in this section merely provide background information related to the present disclosure and may not constitute prior art.

The flow and flow rate of tissue and fluids through an aspiration tube is of interest during operations, including ophthalmic operations. Measurement of the surgical aspiration flow rate may be valuable in that it can provide for safe control of the ophthalmic surgical equipment. In most positive displacement-based systems, flow has been known to be inferred from the cycle frequency, i.e., the rotation rate, of the aspiration pump. However, this inference may be invalid in situations where there are varying pressure differentials within the pump system. The pressure variations may occur as a result of changes in the irrigation-fluid bottle height, changes in the viscosity of the aspirant, and changing occlusion conditions at the distal end of the aspiration tube. For known commercially available vacuum-based aspiration systems no flow measurement has previously been feasible, nor can flow be accurately inferred from the vacuum level. This is because the actual flow rate varies with the viscosity of the aspirant and the occlusion state of the aspiration tube. Thus, direct measurement of the flow rate is difficult to achieve and typically, impractical for vacuum-based systems.

Therefore, it would be desirable to have a viable, low-cost flow sensor that could be inexpensively incorporated into a disposable or reusable system to directly measure flow rate. Such a flow measurement can enable new modes of operation, particularly for vacuum-based systems.

SUMMARY

In accordance with one aspect of the present application, a sensing means is provided for enabling control of aspiration flow rate, which includes an electrode terminal chamber for sensing flow therethrough. The electrode terminal chamber has an inlet in communication with a flow channel for receiving fluid and viscoelastic material aspirated from a surgical site, and an outlet that tapers into a flow channel in communication with an aspiration collection reservoir. The outlet end has a taper that is sufficient to smooth flow and cause viscoelastic material entering the electrode terminal chamber to flow substantially within a center portion of the chamber. The electrode terminal chamber further includes first and second electrode terminals disposed on generally opposite sides of the electrode terminal chamber in a spaced-apart manner. The first and second electrode terminals are positioned at a distance from the center of the chamber that is sufficient to substantially prohibit contact by the electrodes with viscoelastic materials flowing through the chamber's center portion.

In yet another aspect of the present application, an ophthalmic surgical pump system is provided for controlling aspiration flow rate. The system comprises a disposable electrode assembly including an electrode terminal chamber therein, and a flow channel extending through the electrode terminal chamber for receiving fluid and viscoelastic material that is aspirated from a surgical site. The electrode terminal chamber includes a first recessed area, which is spaced from the flow channel extending through the electrode terminal chamber. The chamber also includes a second recessed area, which is spaced from the flow channel extending through the electrode terminal chamber. The electrode terminal chamber further includes an outlet end that tapers into the flow channel, where the outlet end has a taper that is sufficient to direct the flow of viscoelastic material through the center of the chamber and away from the first and second recessed areas. The electrode terminal chamber, further includes a first and second electrode terminals made of a corrosion-resistant, electrically-conductive metal, which are respectively disposed within the first and second recessed areas, proximate to, and spaced a distance from the flow channel. The first electrode terminal and second electrode terminal are spaced at a distance that is sufficient to avoid any viscoelastic material that flows through the chamber, such that flow of viscoelastic materials does not impinge on either of the first and second electrode terminals.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
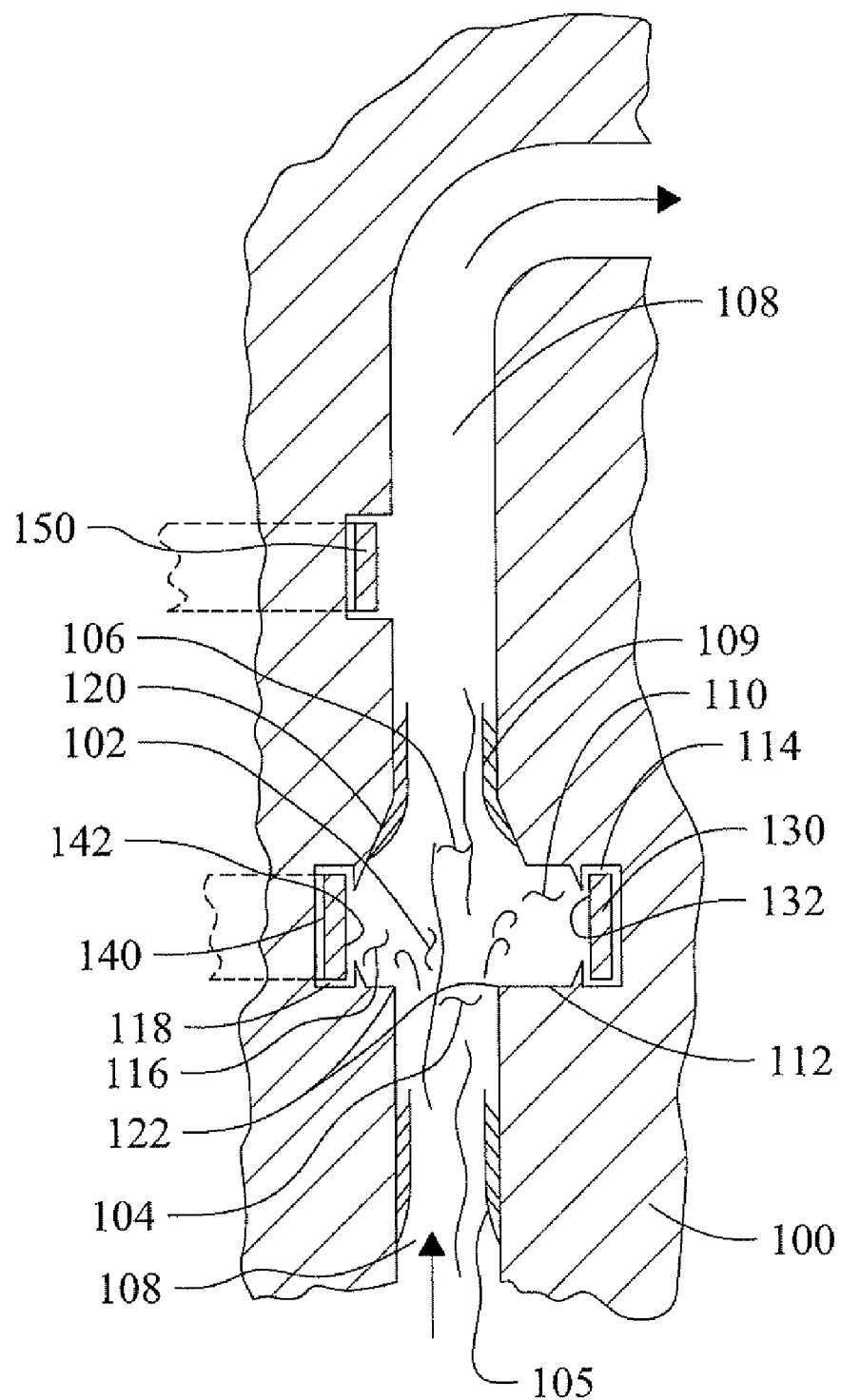
FIG. 1 is a partial cut-away view of a flow channel and sensing chamber, in accordance with the present application.

The following description is merely exemplary in nature and is not intended to limit the present disclosure, application, or uses. It should be understood that throughout the drawings, corresponding reference numerals indicate like or corresponding parts and features.

Ophthalmic surgical aspiration systems can be broadly categorized as flow-based or vacuum-based. Flow-based pump systems attempt to maintain a constant or controlled rate of flow through an aspiration path within specific vacuum ranges. A feedback or control loop may be used to ensure the constancy of the drive system under differing load conditions. An additional feedback control loop may exist between a vacuum sensor in the aspiration line and the motor, to limit the amount of vacuum in the aspiration collection reservoir.

Vacuum-based systems also have feedback control loops, wherein the signal from a vacuum sensor in the aspiration path is compared to the pre-set desired vacuum level. Error signals are then sent to a vacuum generator, such as a proportional value and venturi chamber, to increase or decrease the vacuum level. In certain situations, the emulation of a flow-based pump system by a vacuum-based pump system may be desirable. Such emulation has been described in U.S. Pat. Nos. 6,599,277 and 6,634,237, assigned to Bausch & Lomb Incorporated, which are hereby incorporated by reference. The present application sets forth inventive structure to allow the efficient position of sensors in an aspiration flow path.

The present application discloses various embodiments that provide a solution for ophthalmic aspiration flow rate measurement. The various embodiments preferably utilize an isolated Hall-effect electromagnetic flow meter, which takes advantage of the fact that the saline solution commonly used in ophthalmic surgery is electrically conductive. The Hall-effect involves the development of a voltage potential across conductive fluids flowing between current-carrying conductors, when subjected to a magnetic field. Thus, a voltage can be induced across an aspiration collection reservoir, if a magnetic field is applied. However, the Hall-effect generates a very small electrical signal because of low field sensitivities. Such flow measurement in an ophthalmic surgical pump system includes the application of a magnetic field source or electromagnetic magnet.

It has been found that if viscoelastic material contacts the conductors, a great amount of noise is generated and the flow measurements are interrupted. Therefore, the present application sets forth an inventive arrangement and orientation for placement of the conductors to avoid contact with viscoelastic materials that are in the aspiration flow stream.

Referring to FIG. 1, a first embodiment is shown of a flow measurement device 100 for an ophthalmic surgical pump system for controlling aspiration flow rate. The ophthalmic surgical pump system for providing control of aspiration flow rate includes an electrode terminal chamber 102 having an inlet 104 and an outlet 106. The electrode terminal chamber 102 inlet 104 is in communication with a flow channel 108 for receiving fluid and viscoelastic material aspirated from a surgical site. The electrode terminal chamber outlet 106 is in communication with a flow channel 108 in communication with an aspiration collection reservoir. While the flow channel 108 is shown in a vertical position as shown in FIG. 1, which minimizes the effects of gravity upon flow of fluids through the chamber 102, the flow channel 108 may also be positioned in orientations other than vertical.

The first embodiment of an ophthalmic surgical pump system with a electrode terminal chamber 102 further includes first and second electrode terminals 130 and 140 disposed on generally opposite sides of the electrode terminal chamber 102, and spaced-apart by a predetermined distance relative to the flow channel. In the first embodiment, the flow channel 108 has a width in the range of about 0.030 inches to about 0.050 inches (about 1.2 millimeters to about 2.0 millimeters), and more preferably a width of about 0.038 inches (about 1.5 millimeters). The first and second electrode terminals 130 and 140 are each positioned a predetermined distance from the centerline of the flow channel 108/chamber 102. This distance is sufficient to substantially avoid contact of viscoelastic materials flowing through the flow channel and chambers center portion with the first and second electrode terminals 130 and 140. In the first embodiment, the distance from the respective front surfaces 132 and 142 of terminals 130 and 140 to the centerline of the flow channel 108/chamber 102 is at least about 0.046 inches/1.8 millimeters to about 0.116 inches/4.6 millimeters (or alternatively about 0.030 to about 0.100 inches from the sides of the flow channel 108). Relative to the flow channel width of about 0.030 to 0.050 inches, the first and second electrode terminals 130 and 140 are preferably spaced apart by a predetermined distance of at least about 0.115 inches (about 4.5 millimeters).

The inlet 104 to the electrode terminal chamber 102 preferably has sharp corners 122. The sharp corner 122 formed between surface 112 and the flow channel sidewalls helps guide or direct the viscoelastic material through the center of the electrode terminal chamber 102 along the projection of the flow channel 108. Thus, the sharp corner 122 causes or forces the viscoelastic material to separate from the boundary layer 105 and continue flowing through the center of the electrode terminal chamber 102. The outlet 106 of the electrode terminal chamber 102 further includes a tapered surface 120. The tapered surface 120 is at an angle relative to the flow channel 108 that is sufficient to cause a smooth boundary layer 109 to form along the surface 120, which creates a laminar flow region between the opposing tapered surfaces 120. Viscoelastic material is directed towards the center of the chamber 102 by the sharp corners 122 and urged towards the outlet 106 by tapered surfaces 120, which act as funnels for directing flow through the chamber 102 and towards the outlet 106. The tapered surfaces 120 act as a funnel for directing the flow of fluids and viscoelastic materials through the laminar flow region between the boundary layers 109 depicted in FIG. 1.

The electrode terminal chamber 102 preferably includes first and second recesses 110 and 116 within the electrode terminal chamber 102 configured to receive the first and second electrode terminals 130 and 140 respectively. The first and second recesses 110 and 116 may further include enclosures 114 and 118 that surround the electrodes 130 and 140, which enclosures have a width in the range of about 0.075 inches to about 0.115 inches (about 3.0 millimeters to about 4.5 millimeters). The first and second recesses are symmetrically disposed on opposing sides of the electrode terminal chamber 102, and spaced from the center portion of the chamber 102 by spacing sufficient to minimize viscoelastic material flow from impinging on the first and second electrode terminals 130 and 140. The outlet end 106 has a tapered surface 120 at an angle that is sufficient to direct a substantial amount of flow through the center portion of the chamber, such that flow of viscoelastic materials does not impinge on either of the first and second electrode terminals. Specifically, the outlet end 106 of the chamber 102 has a surface 120 at an angle relative to the flow channel 108 that is sufficient to cause smooth boundary layers 109 to form along the surfaces 120, and create a laminar flow region therebetween. The tapered surfaces 120 and the squared corners 122 cause the viscoelastic material and fluid to flow substantially within a center portion of the chamber 102. The tapered surfaces 120 acts as a funnel for directing the flow of fluids and viscoelastic materials within the laminar flow region and through the outlet 106. Thus, viscoelastic materials aspirated from a surgical site that enter the chamber will flow substantially within a central laminar flow region, and through the outlet. Accordingly, the squared corners 122 at the inlet and tapered surfaces 120 at the outlet of the chamber provide for smoothed flow to avoid contact of viscoelastic materials with the electrode terminals 130 and 140. This is critical, since it has been found that contact of viscoelastic materials or tissues will throw off the signal generated at the electrode terminals, and adversely affect the flow sensing capability of the ophthalmic surgical pump system.

The fluid flowing through the electrode terminal chamber 102 generally comprises an electrically conductive saline solution. Accordingly, the first and second electrode terminals 130 and 140 are arranged opposite one another in a spaced-apart relationship that is sufficient to generate at least one electrical signal indicative of the flow rate of the fluid flowing through the electrode terminal chamber 102. Because the Hall-effect generates a very small electrical signal due to low field sensitivities, the first and second electrode terminals 130 and 140 are plated with a corrosion resistant electrically-conductive metal, to help prolong the electrically conductive characteristics of the terminals. The terminals 130 and 140 are preferably plated with gold, and may also be plated with other materials, such as platinum. The electrode terminal chamber 102 may further include one or more additional electrode terminals, such as terminal 150, which may be used to establish a ground or reference signal for comparison to the at least one signal generated by electrode terminals 130 and 140.

The electrode terminal chamber and flow channel shown in FIG. 1, preferably forms a disposable electrode assembly that is adapted to connect to, or incorporated in an ophthalmic surgical pump system. The first and second electrodes provide at least one signal that is indicative of the flow rate of fluid flowing through the disposable electrode assembly. Such a disposable electrode assembly is preferably used within an ophthalmic surgical pump system.

Figure 2:
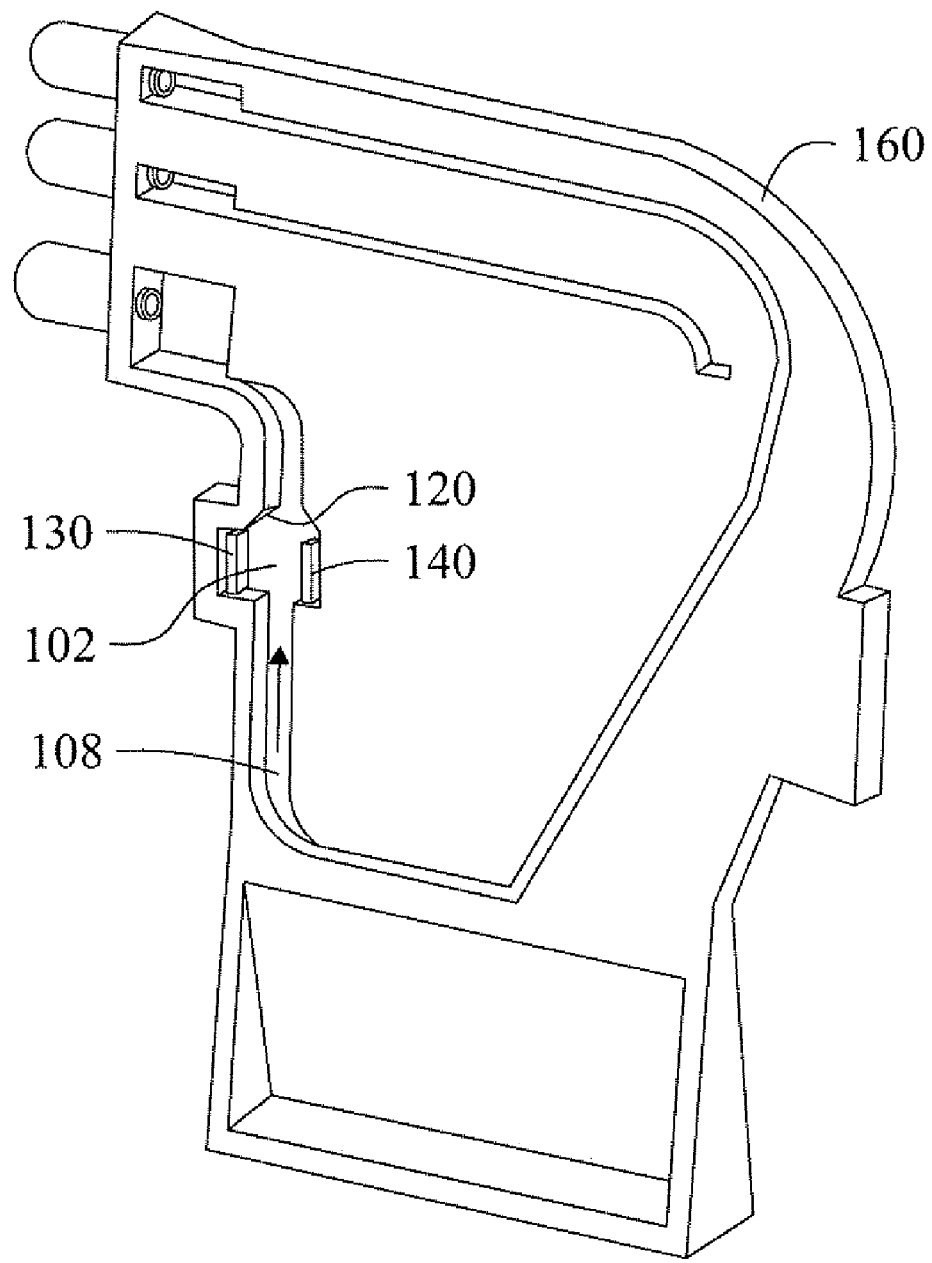
FIG. 2 is a section of a surgical flow measurement device having the sensing chamber, in accordance with one aspect of the present application.
Figure 3:
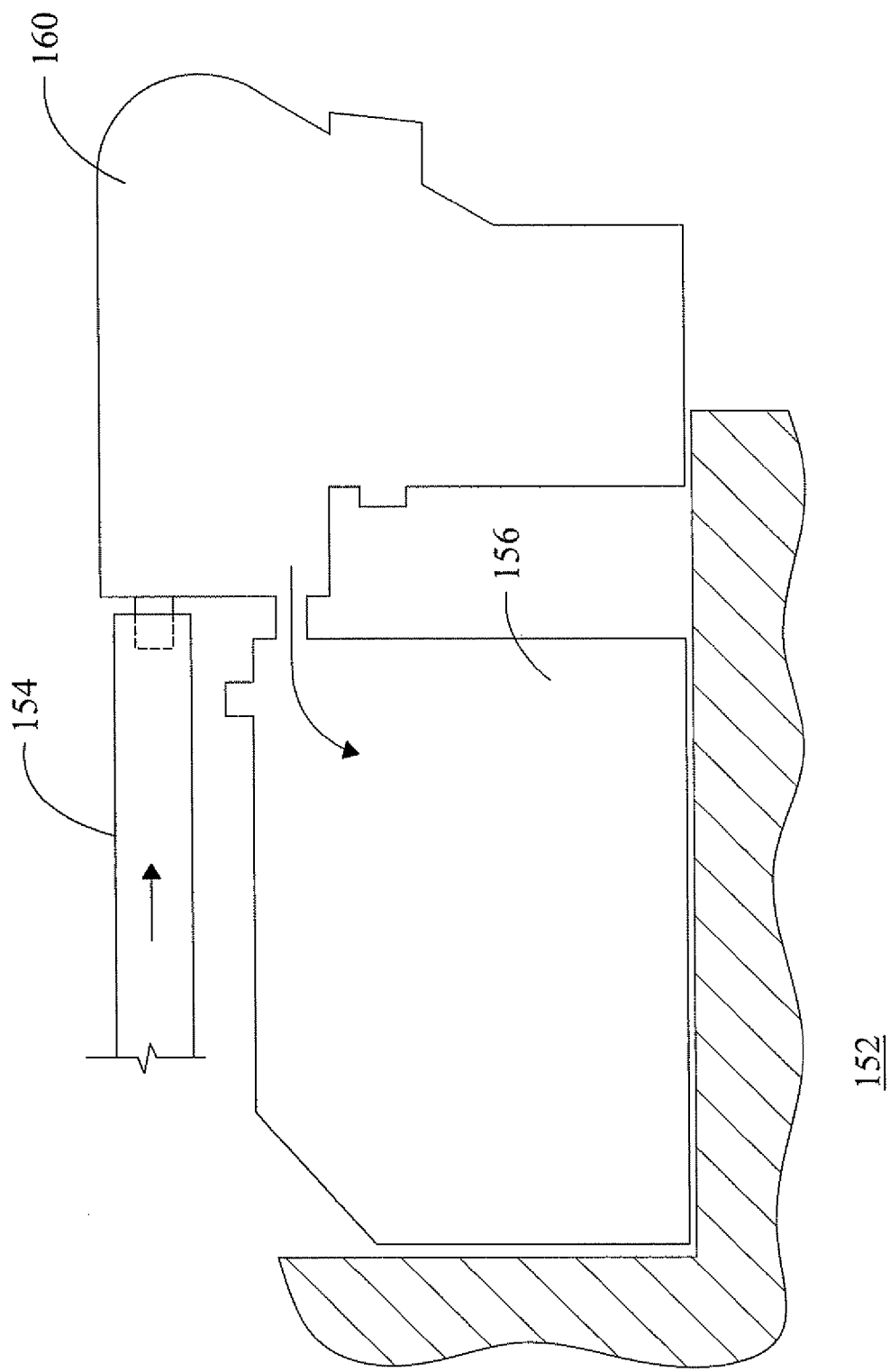
FIG. 3 is a partial elevation view showing a flow measurement device incorporated into a collection cassette, in accordance with an aspect of the present application.

In a second embodiment shown in FIGS. 2 and 3, an ophthalmic surgical pump system is provided for controlling aspiration flow rate. The system comprises a disposable electrode assembly, including an electrode terminal chamber therein, and a flow channel extending through the electrode terminal chamber for receiving fluid and viscoelastic material that is aspirated from a surgical site. The electrode terminal chamber includes a first recessed area, which is spaced from the flow channel extending through the electrode terminal chamber. The chamber also includes a second recessed area, which is spaced from the flow channel extending through the electrode terminal chamber. The electrode terminal chamber further includes an outlet end that tapers into the flow channel, where the outlet end has a taper that is sufficient to direct the flow of viscoelastic material through the center of the chamber and away from the first and second recessed areas. The electrode terminal chamber further includes first and second electrode terminals made of a corrosion-resistant, electrically-conductive metal, which are respectively disposed within the first and second recessed areas, proximate to and spaced a distance from the flow channel. The first and second electrode terminals are spaced at a distance that is sufficient to avoid any viscoelastic material that flows through the chamber, such that flow of viscoelastic materials does not impinge on either of the first and second electrode terminals.

In use, the disposable electrode assembly is preferably connected to an ophthalmic surgical pump system 152, shown in FIG. 3. Control electronics or a processor (not shown), preferably responds to at least one output signal provided by the electrode terminals 130 and 140, to control a proportional valve or venturi chamber (not shown) of a vacuum or venturi pump to emulate a peristaltic pump by maintaining a constant flow rate of fluids and tissues through flow channel 108. Preferably, measurement device 160 of FIG. 2 is incorporated into a disposable cassette 156, as shown in FIG. 3. The preferred embodiment comprises an aspiration path 154 connected to the measurement device 160 and an ophthalmic surgical instrument (not shown), but the flow channel 108 could also include other pathways that allow fluids and tissues to be carried away from the surgical site. A venturi or vacuum pump may be utilized to create a vacuum level for aspirating fluid and tissue from the surgical site of an eye for example, through the collection flow channel 108 to a collection reservoir cassette 156. One commercially available venturi pump that could be adapted to the present application, is a venturi pump sold with Bausch & Lomb Incorporated's Millennium™ or the vacuum system available on the Stellaris™ system. The flow measurement electrode terminals are electrically connected to control circuitry (not shown), for varying the vacuum level of the pump and thereby maintaining a desired flow rate of the fluid and tissue being aspirated from the surgical site.

Preferably, the electrode terminal chamber 102 is included in a rigid-walled cassette 156, so that the cassette will be operable and not collapse during operation when a vacuum level is applied by a venturi pump. One such exemplary collection reservoir is shown in FIGS. 2 and 3. The electrodes 130 and 140 are shown in FIG. 2 and incorporated in a measurement device.

Thus, there has been shown an inventive ophthalmic surgical pump system providing a low-cost aspirant flow meter. In addition, such a system may be used for applications in connection with a vacuum or venturi-based pump system to emulate a positive displacement pump. The sensed flow rate output signal obtained from the electrode terminals 130 and 140 can be used in a feedback control loop to adjust the vacuum level. This feedback control loop is preferably part of control circuitry (not shown) that measures the flow rate and compares that rate to the desired flow rate. If the sense flow rate is lower than desired, a vacuum generator level is increased to generate additional vacuum and increase the flow rate. Conversely, if the flow rate is too high, the vacuum generator level is decreased resulting in a decreased flow rate. In this way of using the control system design, the characteristics of a flow-based pump may be emulated using a vacuum or venturi pump.

What is claimed is:

1. An ophthalmic surgical pump system for providing control of aspiration flow rate, comprising:

an electrode terminal chamber having an inlet in communication with a flow channel for receiving fluid and viscoelastic material aspirated from a surgical site, and an outlet that tapers into a flow, the outlet having a taper angle that is sufficient to smooth flow and cause viscoelastic material entering the electrode terminal chamber to flow substantially within a center portion of the chamber and through the outlet; and first and second electrode terminals disposed on generally opposite sides of the electrode terminal chamber in a spaced-apart manner, the first and second electrode terminals each being positioned a distance from the center of the chamber that is sufficient to substantially avoid contact with viscoelastic materials flowing through the chamber.

2. The ophthalmic surgical pump system of claim 1, further comprising first and second recesses within the electrode terminal chamber configured to receive the first and second electrode terminals, the first and second recesses being symmetrically disposed on opposing sides of the electrode terminal chamber and spaced from the center portion of the chamber by a spacing sufficient to prevent viscoelastic material flow from impinging on the first and second electrode terminals.

3. The ophthalmic surgical pump system of claim 1, wherein the inlet of the electrode terminal chamber includes sharp corners formed between the chamber inlet opening and the flow channel sidewalls, which guide or direct the viscoelastic material through the center of the electrode terminal chamber.

4. The ophthalmic surgical pump system of claim 3, wherein the outlet has a tapered surface at an angle that causes the viscoelastic materials guided through the center of the chamber by the sharp corners to be substantially directed towards the outlet of the chamber, such that flow of viscoelastic materials does not impinge on either of the first and second electrode terminals.

5. The ophthalmic surgical pump system of claim 1, wherein said aspirated fluid comprises an electrically conductive saline solution, and the first and second electrode terminals are arranged opposite one another in a spaced-apart relationship sufficient to generate at least one electrical signal indicative of the flow rate of said fluid flowing through the electrode terminal chamber.

6. The ophthalmic surgical pump system of claim 1, wherein the electrode terminal chamber and flow channel form a disposable electrode assembly that is adapted to connect to an ophthalmic surgical pump system, and the first and second electrodes provide at least one signal indicative of the flow rate of fluid flowing through the disposable electrode assembly.

7. The ophthalmic surgical pump system of claim 1, wherein the first and second electrode terminals are plated with a corrosion resistant electrically-conductive metal.

8. An ophthalmic surgical pump system for providing control of aspiration flow rate, comprising:
    a disposable electrode assembly including a flow channel having an inlet for receiving fluid, tissue, and viscoelastic material aspirated from a surgical site, and an outlet;
    an electrode terminal chamber disposed between the flow channel inlet and outlet, the electrode terminal chamber having an outlet end that tapers into the flow channel, said outlet end having a taper that is sufficient to smooth flow and cause viscoelastic material entering the electrode terminal chamber to flow substantially within a center portion of the chamber and through the outlet;
    first and second electrode terminals disposed on generally opposite sides of the electrode terminal chamber in a spaced-apart manner, the first and second electrode terminals each being positioned at a distance from the center of the chamber that is sufficient to substantially avoid contact between the first and second electrode terminals and viscoelastic materials flowing through the chamber's center portion; and
    wherein the disposable electrode assembly is incorporated in a collection cassette.

9. The ophthalmic surgical pump system of claim 8, further comprising first and second recesses within the electrode terminal chamber configured to receive the first and second electrode terminals, the first and second recesses being symmetrically disposed on opposing sides of the electrode terminal chamber and spaced from the center portion of the chamber by a spacing sufficient to prevent viscoelastic material flow from impinging on the first and second electrode terminals.

10. The ophthalmic surgical pump system of claim 8, wherein the chamber outlet is vertically oriented above the chamber inlet, the chamber outlet including a tapered portion at an angle relative to the flow channel that is sufficient to establish a laminar flow region for directing viscoelastic material through a center portion of the chamber, such that flow of viscoelastic materials does not impinge on either of the first and second electrode terminals.

11. The ophthalmic surgical pump system of claim 8, wherein the inlet of the electrode terminal chamber includes sharp corners formed between the chamber inlet opening and the flow channel sidewalls, which guide or direct the viscoelastic material through the center of the electrode terminal chamber.

12. The ophthalmic surgical pump system of claim 11, wherein the outlet has a tapered surface at an angle that causes the viscoelastic materials guided through the center of the chamber by the sharp corners to be substantially directed towards the outlet of the chamber, such that flow of viscoelastic materials does not impinge on either of the first and second electrode terminals.

13. The ophthalmic surgical pump system of claim 8, wherein said fluid comprises an electrically conductive saline solution, and the first and second electrode terminals are arranged opposite one another in a spaced-apart relationship sufficient to generate at least one electrical signal indicative of the flow rate of said fluid flowing through the electrode terminal chamber.

14. The ophthalmic surgical pump system of claim 8, wherein the electrode terminal chamber and flow channel form a disposable electrode assembly that is adapted to connect to an ophthalmic surgical pump system, and the first and second electrodes provide at least one signal indicative of the flow rate of fluid flowing through the disposable electrode assembly.

15. The ophthalmic surgical pump system of claim 8, wherein the first and second electrode terminals are plated with a corrosion resistant electrically-conductive metal.

16. An ophthalmic surgical pump system for providing control of aspiration flow rate, comprising:
    an electrode assembly including an electrode terminal chamber therein, and a flow channel extending through the electrode terminal chamber for receiving fluid and viscoelastic material that is aspirated from a surgical site, wherein the electrode terminal chamber includes a first recessed area spaced from the flow channel extending through the electrode terminal chamber, a second recessed area spaced from the flow channel extending through the electrode terminal chamber, and an outlet end that tapers into the flow channel, said outlet end having a taper that is sufficient to direct the flow of viscoelastic material through the center of the chamber and away from the first and second recessed areas;
    a first electrode terminal made of a corrosion resistant electrically-conductive metal, disposed within the first recessed area proximate to and spaced a distance from the flow channel;
    a second electrode terminal made of a corrosion resistant electrically-conductive metal, disposed within the second recessed area, proximate to and spaced a distance from the flow channel; and
    wherein the first electrode terminal and second electrode terminal are spaced at a distance that is sufficient to avoid flow of viscoelastic material passing through the chamber, such that flow of viscoelastic materials does not impinge on either of the first and second electrode terminals.

17. The ophthalmic surgical pump system of claim 16, wherein the first and second recesses are symmetrically disposed on opposing sides of the electrode terminal chamber and flow channel extending through the chamber.

18. The ophthalmic surgical pump system of claim 17, wherein the inlet of the electrode terminal chamber includes sharp corners formed between the chamber inlet opening and the flow channel sidewalls, which guide or direct the viscoelastic material through the center of the electrode terminal chamber.

19. The ophthalmic surgical pump system of claim 18, wherein the outlet has a tapered surface at an angle that causes the viscoelastic materials guided through the center of the chamber by the sharp corners to be substantially directed towards the outlet of the chamber, such that flow of viscoelastic materials does not impinge on either of the first and second electrode terminals.

20. The ophthalmic surgical pump system of claim 17, wherein said fluid comprises an electrically conductive saline solution, and the first and second electrode terminals are arranged opposite one another in a spaced-apart relationship sufficient to generate at least one electrical signal indicative of the flow rate of said fluid flowing through the electrode terminal chamber.

\* \* \* \* \*